United States Patent [19]

McFarland

[11] 3,931,174
[45] Jan. 6, 1976

[54] ALKYLMERCAPTOMETHYLQUINOXA-LINE-1,4-DIOXIDES AND OXIDIZED DERIVATIVES THEREOF

[75] Inventor: James W. McFarland, Lyme, Conn.

[73] Assignee: Pfizer Inc., New York, N.Y.

[22] Filed: Jan. 23, 1974

[21] Appl. No.: 435,874

[52] U.S. Cl............................ 260/250 Q; 424/250
[51] Int. Cl.² ...................................... C07D 241/44
[58] Field of Search ................. 260/250 Q, 250 QN

[56] References Cited
UNITED STATES PATENTS
3,803,145  4/1974  Abushanab...................... 260/250 Q
FOREIGN PATENTS OR APPLICATIONS
2,105,112  8/1971  Germany ....................... 260/250 Q
OTHER PUBLICATIONS
Yale, *J. of Med. and Pharm. Chem.,* 6-23, 59, p. 131.

*Primary Examiner*—Donald G. Daus
*Assistant Examiner*—David E. Wheeler
*Attorney, Agent, or Firm*—Connolly and Hutz

[57] ABSTRACT

Novel quinoxaline-1,4-dioxides of the formula

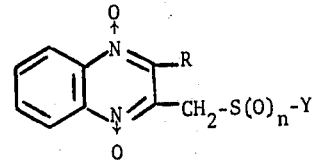

wherein R is hydrogen or methyl;
Y is lower alkyl; and
$n$ is 0, 1, or 2;
methods for their preparation; and their use as antibacterial agents and agents for promoting growth and improving feed efficiency of animals. Additionally, those compounds wherein $n$ is 0 or 1 serve as intermediates for preparation of compounds wherein $n$ is 1 or 2.

10 Claims, No Drawings

ALKYLMERCAPTOMETHYLQUINOXALINE-1,4-DIOXIDES AND OXIDIZED DERIVATIVES THEREOF

BACKGROUND OF THE INVENTION

Field of the Invention

This invention relates to novel quinoxaline-1,4-dioxides useful as antibacterial agents and animal growth promotants. More particularly, the compounds of this invention are represented by formula I:

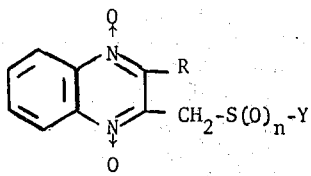

wherein R is selected from the group consisting of hydrogen and methyl;
n is 0 or an integer from 1 to 2; and
Y is lower alkyl.

DESCRIPTION OF THE INVENTION

The search for compounds of improved activity as growth promotants and antibacterial agents has given rise to the preparation and study of a wide variety of quinoxaline-1,4-dioxides. British Pat. No. 1,293,850, published Feb. 21, 1973, describes antibacterial compounds of formula II

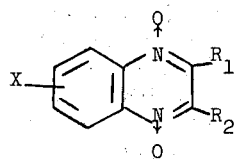

wherein X is a 6-(or7)-position substituent and is inter alia hydrogen, methyl, sulfonamido, N-methyl or N,N-dimethylsulfonamido; $R_1$ is hydrogen, and alkyl of up to 6 carbon atoms; and $R_2$ is $-S-(O)_n-R_3$ wherein $n$ is 0, 1, or 2; and $R_3$ is alkyl of up to 6 carbon atoms, phenyl, benzyl, substituted phenyl or substituted benzyl.

U.S. Pat. No. 3,644,360, issued Feb. 22, 1972 discloses compounds of formula II wherein x is, for example, hydrogen or methyl; $R_1$ is $-CONR'R''$ wherein $R'$ is hydrogen or lower alkyl; $R''$ is inter alia $R'$, hydroxy(lower alkyl), amino lower alkyl, mono-or di(lower alkyl)amino; and $R_2$ is $-CH_2Z$ wherein Z is lower alkythio, lower alkylsulfinyl or lower alkyl sulfonyl.

British Pat. No. 1,308,370, published Feb. 28, 1973, describes compounds of formula II wherein X is as defined above for British Pat. No. 1,293,850; $R_1$ is lower alkyl or phenyl and $R_2$ is $-(CH_2)_m-SO_3H$ wherein m is 0 or 1. It also teaches compounds wherein X is as previously defined; $R_1$ is carbo(lower alkoxy); and $R_2$ is $-CH_2-SH$ or $-CH_2-S(lower alkyl)$.

SUMMARY OF THE INVENTION

It has now been found that quinoxaline-1,4-dioxides of formula I are highly effective against gram positive and gram negative bacteria both in vitro and in vivo and of relatively low acute toxicity compared to the prior art compounds of formula II which are described in British Pat. No. 1,293,850. Additionally, they are effective animal growth promotants, particularly for swine, cattle, and poultry.

The terms "lower alkyl" and "lower alkoxy" as used herein are intended to include alkyl and alkoxy groups containing from 1 to 4 carbon atoms since the reactants having such groups are readily available.

Of particular interest among the compounds of this invention, by reason of their broad spectrum, high potency and relatively low acute toxicity, are compounds of formula I wherein Y is lower alkyl; and R is hydrogen or methyl.

The compounds of this invention wherein R and Y are as defined above, and $n$ is 0 are prepared from the corresponding methyl compounds by a series of reactions comprising (1) bromination (or chlorination) to produce the corresponding bromo (or chloro)methyl derivative; reaction of the bromo (or chloro)methyl derivative with the appropriate lower alkylmercaptan ($HS-CH_2Y$) in the presence of a base to produce the corresponding lower alkylthiomethyl derivative. The corresponding lower alkylsulfinylmethyl and 3-lower alkylsulfonylmethyl derivatives are prepared by oxidation of the 3-lower alkylthiomethyl derivatives.

An alternative procedure comprises treating the bromo (or chloro) methyl derivative with trimethylamine (or other tertiary amine such as pyridine or triethylamine) to provide the corresponding trimethylammonium compound; followed by replacement of the trimethylammonium group by the appropriate lower alkylthio group or substituted lower alkylthio group.

A further procedure comprises preparation of a compound of formula I wherein $n$ and Y are as defined above and R is carbo(lower alkoxy) (British Pat. No. 1,308,370) by one of the above-described procedures followed by hydrolysis of the ester group and thermal decarboxylation of the thus-produced carboxy group.

DETAILED DESCRIPTION OF THE INVENTION

The 3-bromo (or chloro)methyl-2-R substituted-quinoxaline-1,4-dioxide precursors of formula I compounds are readily prepared by direct halogenation of the corresponding 3-methyl-2- R-substituted-quinoxaline-1,4-dioxides. Molecular bromine or chlorine are especially convenient agents to use. One procedure comprises mixing from one to two molar proportions of the 3-methylquinoxaline-2-R-substituted 1,4-dioxide and halogenating agent in chloroform or other chlorinated solvent such as methylene chloride, carbon tetrachloride and chlorobenzene. Additionally, solvents such as formic, sulfuric and acetic acids, and N,N-dimethylformamide can also be used. The reaction is conducted over a temperature range of from about 20°C. to about 120°C. and desirably at from about 60°C. to about 100°C. for periods of from about 1 to about 4 hours.

The trimethylammonium derivatives are then prepared by treating the appropriate 3-bromo(or chloro)-methylquinoxaline-2-R-substituted 1,4-dioxide with trimethylamine. The reaction is conducted in a suitable diluent, or solvent, such as N,N-dimethylformamide, ethanol, benzene, xylene, chloroform, dioxane or tetrahydrofuran at temperatures from about 20°C. to about 100°C., and preferably from about 20°C. to about 60°C. Trimethylamine is bubbled into a stirred mixture of the diluent and appropriate 3-bromo-(or chloro)methylquinoxaline-2-R-substituted-1,4-dioxide until the mixture is saturated. The exothermic reaction is stirred for from about one-half to about 4 hours and the product recovered by filtration or evaporation of the diluent.

Replacement of the trimethylammonium group by lower alkylthio is accomplished by reacting it with the appropriate lower alkyl mercaptan and aqueous sodium or potassium hydroxide. An organic solvent such as chloroform is then added followed by the ([3-(R-substituted)quinoxalin-2-yl]methyl) trimethylammonium bromide (or chloride) 1,4-dioxide. The mixture is thoroughly stirred for from about one to four hours, the organic solvent phase separated and the 3-lower alkylthiomethylquinoxaline-2-R-substituted-1,4-dioxide recovered by removal of the solvent.

The 3-lower alkylthiomethylquinoxaline-1,4-dioxides, in addition to their use as antibacterial agents, are intermediates for the production of the corresponding 3-lower alkylsulfinylmethyl- and 3-lower alkylsulfonyl methylquinoxaline-2-R-substituted-1,4-dioxides by oxidation with hydrogen peroxide or an organic peracid such as peracetic, perphthalic, perbenzoic or m-chlorperbenzoic acid. This last-named peracid is especially useful since the by-product m-chlorobenzoic acid is easily removed. The reaction is conducted in a solvent such as chloroform or methylene chloride at from about 0°C. to about 30°C. until one or two equivalents (depending upon whether the sulfinyl or sulfonyl derivative is desired) of the oxidizing agent is consumed. It is advantageous when producing the sulfinyl derivatives to use equimolar proportions of reactants in order to avoid, or minimize, further oxidation. Oxidation to the sulfinyl stage by means of hydrogen peroxide proceeds somewhat sluggishly. A greater than equimolar proportion of hydrogen peroxide and relatively short reaction times, e.g. up to 1 hour. can, therefore, be used without formation of the sulfonyl derivative.

The oxidation of the sulfonyl stage can also be accomplished by treating the appropriate thio derivative in aqueous media with sodium tungstate and hydrogen peroxide at a temperature of from about 50°C. to about 100°C. The metal compound is generally used at from about 0.0005 to about 0.2 moles and preferably from about 0.0005 to about 0.02 moles per mole of the thio derivative. An excess of hydrogen peroxide is generally used to insure conversion of the tungstate to pertungstate.

The bromo (or chloro) methyl derivative can be reacted with the appropriate lower alkylmercaptan in a reaction inert solvent, such as chloroform, methylene chloride, methanol, ethanol, propanol, in the presence of a base. Representative bases are secondary and tertiary amines such as di(lower alkyl)amines, tri(lower alkyl)amines, pyridine; inorganic bases such as potassium and sodium hydroxides or acetates. A desirable property of the base chosen is that it be soluble in the reaction-inert solvent used to expedite the reaction. The base and mercaptan are generally used in molar proportions of from about 1:1 to about 1.5 : 1.0. The reaction is normally conducted at room temperature to about 50°C. Temperatures outside this range can be used but offer no advantages to the process.

The products of this invention are remarkably effective in treating a wide variety of pathogenic microorganisms and are, therefore, useful as industrial antimicrobials, for example in water treatment, slime-control, paint preservation and wood preservation as well as for topical application purposes as disinfectants.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media, that is, media which have no harmful effect on the active ingredient. For such purposes, it will generally be acceptable to employ concentrations of active ingredients of from about 0.01 percent to about 10 percent by weight based on total composition.

The compounds described herein, in contrast to the usual gram-negative activity of quinoxaline-1,4-dioxides, exhibit broad spectrum activity against both gram-negative and gram-positive bacteria, such as *Staphylococcus aureus*, *Streptomyces pyogenes*, *Escherichia coli*, *Pasteurella multocida* and *Shigella sonnei*.

When used in vivo for such purposes, these novel compounds can be administered orally or parenterally, e.g., by cutaneous or intramuscular injection, at a dosage of from about 1 mg./kg. to about 100 mg./kg. of body weight. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents, in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition. Other methods include mixing with animal feeds, the preparation of feed concentrates and supplements and dilute solutions or suspensions, e.g., a 0.1 percent solution, for drinking purposes.

The addition of a low level of one or more of the herein described compounds of formula I to the diet of healthy animals, both ruminant and non-ruminant, such that these animals receive the product over an extended period of time, at a level of from about 1 mg./kg. to about 100 mg./kg. of body weight per day, especially over a major portion of their active growth period, results in an acceleration of the rate of growth and improves feed efficiency (the number of pounds of feed required to produce a pound gain in weight). Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed.

The feed compositions described herein have been found to be particularly valuable and outstanding in the case of swine. In some instances the degree of response may vary with respect to the sex of the animals. The products may, of course, be administered in one component of the feed or they may be blended uniformly throughout a mixed feed, alternatively as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of the quinoxaline-1,4-dioxides described above. Some of the various components are commonly grains such as ground grain and grain by-products; animal protein substances, such as meat and fish by-products; vitaminaceous mixtures, e.g., vitamine A and D mixtures, riboflavin supplements and other vitamin B complexes; and bone meal, limestone and other inorganic compounds to provide minerals.

The present compounds are advantageously combined in such relative proportions with edible carriers as to provide pre-mixes or concentrates which may readily be blended with standard nutritionally balanced feeds or which may be used themselves as an adjunct to normal feedings.

In the preparation of concentrates a wide variety of carriers such as soybean oil meal, corn gluten meal, cotton seed oil meal, sunflower seed meal, linseed oil meal, corn meal, limestone and corncob meal can be employed to facilitate uniform distribution of the active materials in the finished feed with which the concentrate is blended. The concentrate may be surface coated, if desired, with various proteinaceous materials of edible waxes, such as zein, gelatin, microcrystalline wax and the like to provide a protective film which seals in the active ingredients. The proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e., pre-mixes, suitable for blending by feed manufacturers to produce finished feeds or concentrates of lower potency, the drug content may range from about 0.1 to 50 g. per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.1 to 10 g. per pound of supplement. A particularly useful concentrate is provided by blending 2 g. of drug with 1 pound of limestone or 1 pound of limestone-soybean oil meal (1:1). Other dietary supplements, such as vitamins, minerals, etc., may be added to the concentrates in the appropriate circumstances.

The concentrates described may also be added to animal feeds to produce a nutritionally balanced, finished feed containing from about 5 to about 125 g. of the herein described compounds per ton of finished feed.

In the case of ruminants, the finished feed should contain protein, fat, fiber, carbohydrate, vitamins and minerals, each in an amount sufficient to meet the nutritional requirements of the animal for which the feed is intended. In the case of non-ruminant animals, such as hogs, a suitable feed may contain from about 50 to 80 percent of grains, 3 to 10 percent animal protein, 5 to 30 percent vegetable protein, 2 to 4 percent of minerals together with supplementary vitaminaceous sources.

The in vitro activities are determined under anaerobic conditions in the following manner.

Appropriate serial two-fold dilutions of the compounds are mixed with molten brain-heart infusion agar in sterile petri dishes and allowed to solidify.

The bacterial cells (approximately $10^5-10^6$ cells) are placed on the top of the agar plate with a Steers replicating device. The plates are incubated at 37°C. in the anaerobic conditions achieved by a Gas Pak (BBL, Cockeysville, Ind.). The M.I.C. (minimal inhibitory concentration) is taken as the lowest concentration of drug which completely inhibits bacterial growth.

The in vitro and in vivo activities of compounds within this invention versus *Streptococcus pyogenes* and *Escherichia coli* are presented below:

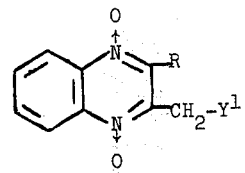

wherein $Y^1$ is $-S(O)_nY$ and $n$ and $Y$ are as defined above.

| | | IN VITRO | | IN VIVO[a] | |
|---|---|---|---|---|---|
| | | | | Survivors (SC route) | |
| | | MIC (mcg./ml.) | | 50 mg./kg. | 25 mg./kg. |
| R | $Y^1$ | Strep. pyogenes | E. coli | Strep pyogenes | E coli |
| H | S—CH₃ | 1.562 | 1.562 | 5/10[b] | 7/10[b] |
| H | S—CH₂CH₂CH₃ | 50 | 50 | 0/10 | 6/10 |
| H | SO—CH₃ | <0.391 | <0.391 | 3/10[b] | 10/10[b] |
| H | SO—CH₂CH₃ | 0.781 | 3.125 | 2/10 | 9/10 |
| H | SO—CH₂CH₂CH₃ | 1.562 | 6.25 | 6/10 | 5/10 |
| H | SO₂—CH₃ | <0.391 | <0.391 | 9/10 | 10/10 |
| H | SO₂—CH₂CH₃ | <0.391 | <0.391 | 10/10 | 10/10 |
| H | SO₂—CH(CH₃)₂ | 1.562 | 0.781 | 10/10 | 9/10 |

-continued

| | | IN VITRO | | IN VIVO[a] | |
| | | MIC (mcg./ml.) | | Survivors (SC route) | |
| | | | | 50 mg./kg. | 25 mg./kg. |
| R | Y' | Strep. pyogenes | E. coli | Strep pyogenes | E coli |
| --- | --- | --- | --- | --- | --- |
| H | $SO_2$—$CH_2CH_2CH_3$ | 3.125 | 25 | 9/10 | 9/10 |
| $CH_3$ | SO—$CH_3$ | 25 | >200 | 2/10 | 1/10 |
| $CH_3$ | $SO_2$—$CH_3$ | 1.562 | 3.125 | 1/10 | 7/10 |

[a]SC = subcutaneous
[b]100 mg./kg.

EXAMPLE 1

2-Methylthiomethylquinoxaline 1,4-Dioxides

To a solution of sodium hydroxide (600 mg., 0.015 m) in water (40 ml.) overlayed with chloroform (40 ml.) was added methylmercaptan (0.72 g, 0.015 m) with stirring. The [(2-quinoxalinyl)methyl]trimethylammonium bromide 1,4-dioxide (5 og., 0.015 m) was added to the methylmercaptan solution in small portions over a 15 minute period. The mixture was stirred for 20 minutes and the chloroform phase separated. Fresh chloroform (40 ml.) was added to the aqueous reaction mixture which was then stirred for a half hour, the chloroform phase separated and this operation repeated once again. The combined chloroform phases were evaporated to dryness under reduced pressure and the residue triturated with hexane (30 ml.). Filtration and drying of the solid gave 2.86 g. (75 percent yield) of the title product, m.p. 118°–119°C. dec.).

The [(2-quinoxalinyl)methyl]trimethylammonium bromide 1,4-dioxide was prepared as follows:

To a stirred solution of 2-methylquinoxaline 1,4-dioxide (213 g., 1.2 m) in acetic acid (700 ml.) at 85°–90°C., was added a solution of bromine (195 g., 1.2 m) in acetic acid (500 ml.) over a period of 15 minutes. The reaction mixture is heated and stirred at 85°–90°C. for another half hour and then cooled to room temperature. The solid which separated was filtered off and then slurried in chloroform (1.5 liters). Saturated aqueous sodium bicarbonate solution was gradually added to the slurry with good stirring until the solid dissolved. The chloroform phase was separated and dried over anhydrous sodium sulfate. Trimethylamine (1.5 m) was then bubbled into the chloroform solution over a one hour period at ambient temperature and the resulting solid was separated by filtration, washed with chloroform (3 × 600 ml.) and dried. yield 215 g. (68 percent): m.p. 223°C.

The related compound, (3-methyl-2-quinoxalinyl)-methyltrimethylaminonium bromide, was prepared as follows:

To a solution of 2,3-dimethylquinoxaline 1,4-dioxide (570 g., 3.0 m) in dichloromethane (3000 ml.) at room temperature was added dropwise a solution of bromine (160 g., 1.0 m) in dichloromethane (1000 ml.) over a period of 90 minutes. After standing overnight at room temperature, the mixture was filtered. The filtrate was washed with saturated sodium bicarbonate solution (3 × 300 ml.), dried over anhydrous sodium sulfate, and filtered. The filtrate was then cooled to −5°C. and anhydrous trimethylamine gas (75 g.) was passed through. The resulting solution was allowed to stand at room temperature for an hour. It was then heated to the boiling point, and filtered hot to furnish the title compound: m.p. 198°–199°C; yield, 193 g. (58.9 percent of theory based on bromine used). It was purified by crystallization from methanol; m.p. 209°–212°C.

The compounds listed below are prepared following the above procedure but using the appropriate mercaptan reactant (HS-Y) in place of methylmercaptan.

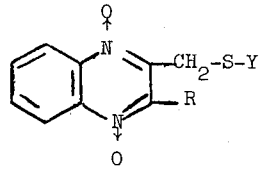

| R | Y | m.p. (°C) | % Yield |
| --- | --- | --- | --- |
| H | $CH_2CH_3$ | 139–140 | 70 |
| H | $CH_2CH_2CH_3$ | 117–119 | 30 |

EXAMPLE 2

2-Methyl-3-Methylthiomethylquinoxaline-1,4-Dioxide

Following the procedure of Example 1,(3-methyl-2-quinoxalinyl) methyltrimethylammonium bromide, 1,4-dioxide was converted to the title compound in 36.1 percent yield; m.p. 95°–96°C.

The (3-methyl-2-quinoxalinyl)methyltrimethylammonium bromide 1,4-dioxide was prepared as follows:

To a solution of 2,3-dimethylquinoxaline 1,4-dioxide (570 g., 3.0 m) in dichloromethane (3000 ml.) at room temperature was added dropwise a solution of bromine (160 g., 1.0 m) in dichloromethane (1000 ml.) over a period of 90 minutes. After standing overnight at room temperature, the mixture was filtered. The filtrate was washed with saturated sodium bicarbonate solution (3 × 300 ml.), dried over anhydrous sodium sulfate, and filtered. The filtrate was then cooled to −5°C. and anhydrous trimethylamine gas (75 g.) was passed through. The resulting solution was allowed to stand at room temperature for an hour. It was then heated to the boiling point, and filtered hot to furnish the title compound: m.p. 198°–199°C; yield, 193 g. (58.9 percent of theory based on bromine used). It was purified by crystallization from methanol; m.p. 209°–212°C.

EXAMPLE 3

2-Methylsulfinylmethylquinoxaline 1,4-Dioxide

A solution of 2-methylthiomethylquinoxaline 1,4-dioxide (2.0 g., 0.009 m) in acetic acid (14 ml.) was cooled to 15°C. while hydrogen peroxide (4 ml. of 30 percent) was added dropwise. The mixture was stirred for 35 minutes and then poured into water (80 ml.) The aqueous solution was extracted with chloroform (5 × 20 ml.), the chloroform extracts combined, dried ($Na_2SO_4$) and evaporated under reduced pressure to an oil Trituration of the oil with hexane (15 ml.) gave 860 mg. (23 percent yield) of product: m.p. 167°–168°C.

In like manner, 2-methyl-3-methylthiomethylquinoxaline 1,4-dioxide is converted to 2-methyl-3-methylsulfinylmethylquinoxaline 1,4-dioxide, m.p. 135°–136°C., in 13.1 percent yield.

EXAMPLE 4

2-Ethylsulfinylmethylquinoxaline 1,4-Dioxide

A solution of m-chloroperbenzoic acid (9.4 g., 0.0465 m of 85 percent material) in chloroform (75 ml.) was added dropwise to a solution of 2-ethylthiomethylquinoxaline 1,4-dioxide (10.98 g. 0.0465 m) in chloroform (100 ml.). The mixture was stirred for one hour and then added dropwise, with stirring, to diethyl ether (1.1 liters). The yellow solid which precipitated was filtered off, washed with diethyl ether (50 ml.) and then with hexane (100 ml.) and dried. Yield = 8.8 g., 75 percent of product: m.p. 145°–147°C.

By means of this procedure, 2-n-propylthiomethylquinoxaline 1,4-dioxide is converted in 73 percent yield to 2-n-propylsulfinylmethylquinoxaline 1,4-dioxide, m.p. 137°–139°C.

EXAMPLE 5

2-Methylsulfonylmethylquinoxaline 1,4-Dioxide

Hydrogen peroxide (25 ml. of 30 percent) was added over a fifteen minute period to a solution of 2-methylthiomethylquinoxaline 1,4-dioxide (13 g., 0.005 m) in acetic acid (100 ml.) cooled to 15°C. The mixture was then stirred overnight at room temperature and the precipitation which formed was separated by filtration. The filtrate was added dropwise to diethyl ether (500 ml.) and the resulting solid filtered off, washed with diethyl ether and dried to give 15 g. of product (57 percent yield): m.p. 225°C.

EXAMPLE 6

2-Ethylsulfonylmethylquinoxaline-1,4-Dioxide

To a solution of sodium tungstate dihydrate (250 mg.) in water (800 ml.) was added 2-(ethylthiomethyl)quinoxaline 1,4-dioxide (53.65 g. 0.2 m). Hydrogen peroxide (57 ml. of 30 percent) was added to the slurry dropwise over a period of 20 minutes. The reaction mixture gradually became a reddish solution and its temperature rose to 33°C. It was then heated at 70°C. (internal temperature) for 1.5 hours and then cooled. The solid which formed was filtered off and dried: 33.0 g. (55 percent yield); m.p. 204°–205°C.

EXAMPLE 7

The following compounds were prepared from corresponding thio compounds by the procedures of Examples 4, 5, or 6.

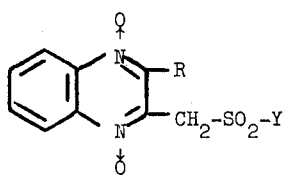

| R | Y | m.p. (°C.) | % Yield | Procedure |
|---|---|---|---|---|
| H | CH(CH$_3$)$_2$ | 177–178 | 13 | 4 |
| H | CH$_2$CH$_2$CH$_3$ | 156–159 | 45 | 4 |
| CH$_3$ | CH$_3$ | 210–212 | 72.4 | 5 |
| CH$_3$ | CH$_2$CH$_3$ | 169–170 | 36 | 6 |
| CH$_3$ | CH$_2$CH$_2$CH$_3$ | 128–130 | 20 | 6 |

EXAMPLE 8

2-Methylthiomethyl-3-carbomethoxyquinoxaline 1,4-Dioxide

Triethylamine (123 ml.) was added to a solution of 2-bromomethyl-3-carbomethoxyquinoxaline 1,4-dioxide (254 g., 0.81 m) in chloroform (1 liter) at room temperature. Methylmercaptan was bubbled slowly through the mixture for 1 hour. The temperature rose to 48°C. The reaction mixture was washed twice successively with hydrochloric acid (250 ml. of N HCl), sodium bicarbonate solution (3 × 250 ml. of 5 percent), and water (2 × 250 ml.). The chloroform solution was dried over anhydrous sodium sulfate and was then evaporated to give an oil which solidified on standing overnight; (124 g., 55 percent yield): m.p. 84°–88°C.

The bromomethyl ester reactant was prepared by adding bromine (64 ml., 128 m) to a thick slurry of 2-methyl-3-carbomethoxyquinoxaline 1,4-dioxide (300 g., 1.28 m) in N,N-dimethylformamide (473 ml.) over a 2 hour period. The mixture was stirred during the addition and for 3 days thereafter at ambient temperature. Ice water (10 liters) was added to the mixture and the product extracted with chloroform (1 liter). The chloroform extract was dried and concentrated to a thick oil. The oil was poured into diethyl ether (3 liters) and the resulting solid separated by filtration and dried. yield 282 g. (70 percent); m.p. 122°–124°C. (dec.)

In like manner the following compounds are prepared but substituting ethylmercaptan and n-propylmercaptan for methylmercaptan:
2-ethylthiomethyl-3-carbomethoxyquinoxaline 1,4-dioxide. (71.75 percent yield), as a brownish oil:
2-n-propylthiomethyl-3-carbomethoxyquinoxaline 1,4-dioxide (<100 percent yield), as a brownish oil.

EXAMPLE 9

2-Methylsulfinylmethyl-3-Carbomethoxy-quinoxaline 1,4-Dioxide

A solution of m-chloroperbenzoic acid (9.4 g., 0.0465 m of 85 percent material) in chloroform (75 ml.) was added dropwise to a solution of 2-methylthiomethyl-3-carbomethoxyquinoxaline 1,4-dioxide (13.0 g. 0.0465 m) in chloroform (100 ml.). The mixture was stirred for one hour and then added dropwise, with stirring, to diethyl ether (1.1 liters). The yellow solid which precipitated was filtered off, washed with diethyl ether (50 ml.) and then with hexane (100 ml.) and dried. Yield = 13.4 g., 97 percent of product: m.p. 141°–142°C.

EXAMPLE 10

2-Methylsulfonylmethyl-3-Carbomethoxyquinoxaline 1,4-Dioxide

To a solution of 2-methylthiomethyl-3-carbomethoxyquinoxaline 1,4-dioxide (124 g., 0.443 m) in chloroform (1000 ml.) was added m-chloroperbenzoic acid (196 g., 0.973 m of 85 percent material) in small portions over a 2 hour period. The mixture was stirred until it cooled to room temperature. The solid which formed was filtered off, washed with diethyl ether (800 ml.) and dried to give 65.6 g. of solid melting at 202°–203°C. The filtrate of the reaction mixture was concentrated to small volume and the concentrate slurried in diethyl ether (800 ml.) The resulting solid was filtered off, washed with diethyl ether, and dried to give 56.9 g.; melting at 190°–193°C. total yield 122.5 g. (89 percent).

The remaining products of Example 8 are oxidized in like manner to give:
2-ethylsulfonylmethyl-3-carbomethoxyquinoxaline 1,4-dioxide (35.7 percent yield); m.p. 169°–170°C.;
2-n-propylsulfonylmethyl-3-carbomethoxyquinoxaline 1,4-dioxide (20 percent yield); m.p. 128°–130°C.

EXAMPLE 11

By the procedures of Examples 3 and 4 the following compounds are prepared from appropriate reactants

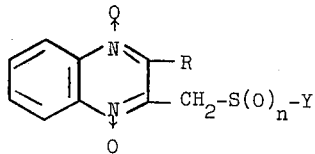

| R | n | Y |
|---|---|---|
| H | 0 | n—C₄H₉ |
| H | 1 | n—C₄H₉ |
| H | 2 | n—C₄H₉ |
| CH₃ | 0 | n—C₄H₉ |
| CH₃ | 1 | n—C₄H₉ |
| CH₃ | 2 | n—C₄H₉ |
| COOC₂H₅ | 0 | CH₃ |
| COO(n—C₄H₉) | 0 | CH₃ |
| COO(n—C₄H₉) | 1 | CH₃ |
| COO(n—C₄H₉) | 2 | CH₃ |
| CH₃ | 0 | C₂H₅ |
| COOCH₃ | 2 | n—C₄H₉ |
| COO(n—C₄H₉) | 0 | n—C₄H₉ |
| COO(n—C₄H₉) | 1 | n—C₄H₉ |
| CH₃ | 1 | C₂H₅ |

EXAMPLE 12

2-Ethylsulfonylmethylquinoxaline 1,4-Dioxide

A slurry of 2-ethylsulfonylmethyl-3-carbomethoxyquinoxaline-1,4-dioxide (28.2 g., 0.087 m) and 0.5 N sodium hydroxide (280 ml.) was stirred at room temperature for 30 minutes. It was then filtered and the filtrate acidified to pH 3 with 6N hydrochloric acid. The resulting slurry was heated in an oil bath (bath temperature 120°C.) for 30 minutes. It was removed from the oil bath, allowed to cool to room temperature and the solid filtered off: 22.2 g. (95 percent yield); m.p. 216°C.

In like manner, the 3-carbo(lower alkoxy)quinoxaline-1,4-dioxides of Examples 8–11 are converted to their corresponding decarboxylated derivatives.

What is claimed is:

1. A compound of the formula

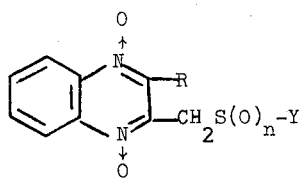

wherein R is selected from the group consisting of hydrogen and methyl;
Y is lower alkyl; and
n is 0 or an integer from 1 to 2.

2. A compound according to claim 1 wherein R is hydrogen.

3. A compound according to claim 1 wherein R is methyl.

4. A compound according to claim 2 wherein n is 0.

5. A compound according to claim 2 wherein n is 2.

6. A compound according to claim 3 wherein n is 2.

7. The compound according to claim 4 wherein Y is ethyl.

8. The compound according to claim 5 wherein Y is methyl.

9. The compound according to claim 5 wherein Y is ethyl.

10. The compound according to claim 6 wherein Y is methyl.

* * * * *